US009243054B2

(12) United States Patent
Burioni et al.

(10) Patent No.: US 9,243,054 B2
(45) **Date of Patent: *Jan. 26, 2016**

(54) MONOCLONAL ANTIBODIES HAVING HOMOSUBTYPE CROSS-NEUTRALIZATION PROPERTIES AGAINST INFLUENZA A VIRUSES SUBTYPE H1

(75) Inventors: Roberto Burioni, Rimini (IT); Massimo Clementi, Milan (IT)

(73) Assignee: POMONA RICERCA S.R.L., Turin (IT)

( * ) Notice: Subject to any disclaimer, the term of this patent is extended or adjusted under 35 U.S.C. 154(b) by 718 days.

This patent is subject to a terminal disclaimer.

(21) Appl. No.: 12/994,746

(22) PCT Filed: May 27, 2009

(86) PCT No.: PCT/IB2009/052212

§ 371 (c)(1), (2), (4) Date: Nov. 24, 2010

(87) PCT Pub. No.: WO2009/144667

PCT Pub. Date: Dec. 3, 2009

(65) Prior Publication Data

US 2011/0076265 A1 Mar. 31, 2011

(30) Foreign Application Priority Data

May 27, 2008 (IT) .............................. TO2008A0398

(51) Int. Cl.
*C12N 15/63* (2006.01)
*C07K 16/10* (2006.01)

(52) U.S. Cl.
CPC ......... *C07K 16/1018* (2013.01); *C07K 2317/21* (2013.01); *C07K 2317/55* (2013.01); *C07K 2317/56* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 4,946,778 | A | 8/1990 | Ladner et al. |
| 5,245,015 | A | 9/1993 | Fung et al. |
| 6,057,421 | A | 5/2000 | Muller et al. |
| 6,964,199 | B2 | 11/2005 | Lee et al. |
| 8,367,061 | B2 | 2/2013 | Burioni et al. |
| 8,486,406 | B2 | 7/2013 | Burioni et al. |
| 8,623,363 | B2 | 1/2014 | Burioni et al. |
| 2003/0100741 | A1 | 5/2003 | Muller et al. |
| 2004/0224310 | A1 | 11/2004 | McGready |
| 2005/0080240 | A1 | 4/2005 | Kunert et al. |
| 2005/0221298 | A1 | 10/2005 | Muller et al. |
| 2008/0014205 | A1 | 1/2008 | Horowitz et al. |

FOREIGN PATENT DOCUMENTS

| | | |
|---|---|---|
| EP | 0621339 | 10/1994 |
| EP | 0675199 | 10/1995 |
| WO | 84/00687 | 3/1984 |
| WO | 92/15885 | 9/1992 |
| WO | 94/09136 | 4/1994 |
| WO | 00/05266 | 2/2000 |
| WO | 0246235 | 6/2002 |
| WO | 02/055560 | 7/2002 |
| WO | 03/064473 | 8/2003 |
| WO | 2007/134327 | 11/2007 |
| WO | 2008/033159 | 3/2008 |
| WO | 2008/093280 | 8/2008 |
| WO | 2009/037297 | 3/2009 |
| WO | 2009/115972 | 9/2009 |
| WO | 2009/144667 | 12/2009 |
| WO | 2010/073204 | 7/2010 |
| WO | 2010/140114 | 12/2010 |
| WO | 2011/117848 | 9/2011 |

OTHER PUBLICATIONS

Li, B. et al., Preparation of anti-idiotypic antibody against avian influenza virus subtype H9 2005 Cell Mol Immunol. Vol, 2(2):155-7.*
Knight et al., Hum Antibodies Hybridomas. Jul. 1992:3(3)129-36 abstract only.*
Asanuma et al., Biochem Biophys Res Comm 2007 vol. 366—pp. 445-449.*
Sui, J. et al. Structural and functional bases for broad-spectrum neutralization of avian and human influenza A viruses, Nature Structural and Molecular Biology, vol. 16, No. 3, pp. 265-273, Mar. 1, 2009.
Written Opinion for PCT Application PCT/IB2010/052434 filed on Jan. 6, 2010, in the name of Pomona Biotechnologies LLC; mail date: Sep. 14, 2010.
International Search Report for PCT Application PCT/IB2010/052434 filed on Jun. 1, 2010, in the name of Pomona Biotechnologies LLC; mail date: Sep. 14, 2010.
International Search Report for PCT Application PCT/IB2008/050307 filed on Jan. 29, 2008, in the name of Pomona Biotechnologies LLC; mailing date: Sep. 9, 2008.
International Preliminary Report on Patentability issued for PCT Application No. PCT/IB2008/050307 filed on Jan. 29, 2008 in the name of Pomona Biotechnologies LLC; mailing date: Apr. 30, 2009.
Written Opinion issued for PCT Application No. PCT/IB2008/050307 filed on Jan. 29, 2008 in the name of Pomona Biotechnologies LLC; mailing date: Sep. 9, 2008.

(Continued)

*Primary Examiner* — Shanon A Foley
*Assistant Examiner* — Myron Hill
(74) *Attorney, Agent, or Firm* — Steinfl & Bruno LLP

(57) ABSTRACT

A monoclonal antibody directed against the influenza A virus is described, which is capable of binding human and animal isolates of influenza A viruses expressing the H1-subtype hemagglutinin. A preferred embodiment is the antibody designated as Fab49, which shows a neutralizing activity against a plurality of influenza A virus isolates expressing the H1-subtype hemagglutinin, including animal-derived isolates. Anti-idiotype antibodies directed against the monoclonal antibody of the invention, immunogenic or vaccine compositions comprising the monoclonal antibody of the invention are also described, as well as therapeutic, prophylactic and diagnostic applications for the monoclonal antibody of the invention. The monoclonal antibody of the invention can also be employed for testing antibody preparations to be used as vaccines.

2 Claims, 3 Drawing Sheets

(56) References Cited

OTHER PUBLICATIONS

PCT International Search Report for PCT Application PCT/IB2009/051068 filed on Mar. 16, 2009 in the name of Pomona Biotechnologies LLC; mailing date: Aug. 31, 2009.
PCT Written Opinion (PCT Rule 43bis.1) for PCT/IB2009/051068 filed on Mar. 16, 2009 in the name of Pomona Biotechnologies LLC; mailing date: Aug. 31, 2009.
PCT Search Report for International Application PCT/IB2009/055867 filed on Dec. 21, 2009 in the name of Bait Biotechologie Applicate Italiane S.R.L.; mailing date: Mar. 31, 2010.
PCT Written Opinion for PCT/IB2009/055867 filed Dec. 21, 2009 in the name of Bait Biotechologie Applicate Italiane S.R.L.; mailing date: Mar. 31, 2010.
PCT International Search Report for PCT/IT2003/000032 (WO 03/064473) filed Jan. 29, 2003 in the name of Roberto Burioni.
PCT International Search report for PCT/US2001/045221 (WO 02/055560) filed Nov. 30, 2001 in the name of the Government of the United States of America, as represented by the Secretary Department of Health and Human Services.
Boudet, F. et al., Anti-idiotypic to the third variable domain of gp120 induce an anti-HIV response in mice, Virology 1994, pp. 176-188.
Braibant, M. et al., Antibodies to conserved epitopes of the HIV-1 envelope in sera from long-term non-progressors: prevalence and association with neutralizing activity, AIDS 2006, 20: 1923-1930.
Bugli, F., et al., Mapping B-cell epitopes of hepatitis C virus E2 glycoproteins using human monoclonal antibodies from phage display libraries, Journal of Virology 2001, 75: 9986-9990.
Burioni, R., I Treponemi Intestinali Umani: Tesi per il conseguimento del dottorato di ricera in scienze microbiologiche di, 1993, 157, (Italian text with English abstract).
Grant, M., et al., The anti-idiotypic antibody 1F7 selectively inhibits cytotoxic T cells activated in HIV-1 infection, Immunology and Cell Biology 2000, 78: 20-27.
Hariharan, K., et al., Analysis of the cross-reactive anti-gp120 antibody population in human immunodeficiency virus-infected asymptomatic individuals, Journal of Virology 1993, 67: 953-960.
Humbert, M., et al., Mimotopes selected with antibodies from HIV-1-neutralizing long-term non-progressor plasma, Eur. J. Immunol. 2007, 37: 501-515.
Kasai, Y., et al., Molecular cloning of murine monoclonal anti-idiotypic Fab, Journal of Immunological Methods 1992, 155: 77-89.
Kunert, R., et al., Molecular characterization of five neutralizing anti-HIV type 1 antibodies: identification of nonconventional D segments in human monoclonal antibodies 2G12 and 2F5, AIDS Research and Human Retroviruses 1998, 14: 1115-1128.
McMichael, AJ, HIV vaccines, The Annual Review of Immunology 2006, 24: 227-255.
Müller, S., et al., Generation and specificity of monoclonal anti-idiotypic antibodies against human HIV-specific antibodies, The Journal of Immunology 1991, 147: 933-941.
Müller, S., et al., Stimulation of antiviral antibody response in SHIV-IIIB-infected macaques, Scand. J. Immunol. 2001, 54: 383-395.
Müller, S., et al., Stimulation of HIV-1-neutralizing antibodies in simian HIV-IIIB-infected macaques, PNAS 1998, 95: 276-281.
Pantophlet, R., et al., GP120: Target for neutralizing HIV-1 antibodies, The Annual Review of Immunology 2006, 24: 739-769.
Wang, H., et al., Human monoclonal and polyclonal anti-human immunodeficiency virus-1 antibodies share a common clonotypic specificity, Eur. J. Immunol. 1992, 22: 1749-1755.
Wang, H., et al., Identification of an idiotypic peptide recognized by autoantibodies in Human immunodeficiency Virus-1 infected individuals, J. Clin. Invest. 1995, 96: 775-780.
Nguyen, HH., et al., Heterosubtypic Immunity to Influenza A Virus Infection Requires B Cells but not CD8+ Cytotoxic T Lymphocytes, The Journal of Infectious Diseases 2001, 183: 368-376.
Rangel-Moreno, J., et al., B Cells Promote Resistance to Heterosubtypic Strains of Influenza via Multiple Mechanisms, The Journal of Immunology 2008, 180: 454-463.

Smirnov, Y. et al., "An epitope shared by the hemagglutinins of H1, H2, H5, and H6 subtypes of influenza A virus." ACTA Virologica 43(4): 237-244 (1999).
Smirnov, Y. et al., "Prevention and treatment of bronchopneumonia in mice caused by mouse-adapted variant of avian H5N2 influenza A virus using a monoclonal antibody against conserved epitope in the HA stem region." Archives of Virology 145(8): 1733-1741 (2000).
Throsby, M. et al., "Heterosubtypic neutralizing monoclonal antibodies cross-protective against H5N1 and H1N1 recovered from human IgM+ memory B cells." PLOS ONE 3(12): 1-15 (2008).
Ziegler, T. et al., "Type- and subtype-specific detection of influenza viruses in clinical specimens by rapid culture assay." Journal of Clinical Microbiology 33(2): 318-321 (1995).
Burton, Mouse primers for fab amplification: original set, Phage Display Manual, 2001, A1.10.
Tarr, A.W. et al., "Determination of the human antibody response to the epitope defined by the hepatitis C virus-neutralizing monoclonal antibody AP33", Journal of General Virology 2007, 88, 2991-3001.
Tarr, A.W. et al., "Characterization of the Hepatitis C Virus E2 Epitope Defined by the Broadly Neutralizing Monoclonal Antibody AP33", Hepatology 2006, 43:3, 592-601.
Johansson, D.X. et al., "Human combinatorial libraries yield rare antibodies that broadly neutralize hepatitis C virus", PNAS 2007, 104:41, 16269-16274.
Burioni, R. et al., "Nonneutralizing Human Antibody Fragments against Hepatitis C Virus E2 Glycoprotein Modulate Neutralization of Binding Activity of Human Recombinant Fabs", Virology 2001, 288, 29-35.
Restriction Requirement issued for U.S. Appl. No. 13/141,071, filed Jun. 20, 2011 in the name of Roberto Burioni et al.; mailing date: Nov. 14, 2011.
Non-Final Office Action issued for U.S. Appl. No. 13/141,071 filed on Jun. 20, 2011 in the name of Roberto Burioni et al.; mail date: Mar. 9, 2012.
Non-Final Office Action issued for U.S. Appl. No. 12/524,816 filed on Jul. 28, 2009 in the name of Roberto Burioni et al. mail date: Jul. 21, 2011.
Restriction Requirement issued for U.S. Appl. No. 12/524,816, filed on Jul. 28, 2009 in the name of Roberto Burioni et al. mail date: Apr. 5, 2011.
Geretti AM, editor. De Luca, A., Antiretroviral Resistance in Clinical Practice. London: Mediscript; 2006, Chapter 12.
"NIH AIDS Research & Reference Reagent Program, Reagent Information, U87.CD4", https://www.aidsreagent.org/reagentdetail.cfm?t=cell_lines&id=20; Jun. 15, 2011, n.p.; retrieved from web. Jan. 23, 2012.
"NIH AIDS Research and Reference Reagent Program, About the Program" https://www.aidsreagent.org/about_program.cfm, n.d.; n.p.; retrieved from web. Jan. 23, 2012.
Chen, C. et al., Enhancement and destruction of antibody function by somatic mutation: unequal occurrence is controlled by V gene combinatorial associations, EMBO J. 1995, 14(12): 2784-2794.
Bansal, G.P., A summary of the workshop on passive immunization using monoclonal antibodies for HIV/AIDS, held at the National Institute of Allergy and Infectious Diseases, Bethesda, Mar. 10, 2006, 2007, Biol. 35: 367-371.
Trkola, A. et al. Delay of HIV-1 rebound after cessation of antiretroviral therapy through passive transfer of human neutralizing antibodies, Nat. Med. 2005, 11(6): 615-622.
Montefiori, D.C., Neutralizing antibodies take a swipe at HIV in vivo, Nat. Med. 2005,11(6): 593-594.
Haigwood, N.L., Predictive value of primate models for AIDS, AIDS Rev. 2004:187-198.
Staprans, S.I. et al. The roles of nonhuman primates in the clinical evaluation of candidate AIDS vaccines, Exp. Rev. Vacc. 2004, 3(4): S5-S32.
Winkler, K., et al., Changing the antigen binding specificity by single point mutations of an anti-p24 (HIV-1) antibody, J. Immunol. 2000, 165: 4505-4514.
Stamatatos, L. et al., Neutralizing antibodies generated during natural HIV-1 infection: good news for an HIV-1 vaccine? Nature Medicine, Aug. 2009, vol. 15, No. 8, pp. 866-870.

(56) References Cited

OTHER PUBLICATIONS

Rudikoff, S. et al., Single amino acid substitution altering antigen-binding specificity, Proc. Natl. Acad. Sci. USA, Mar. 1982, vol. 79, pp. 1979-1983.
Eren, R. et al., Preclinical Evaluation of Two Neutralizing Human Monoclonal Antibodies against Hepatitis C Virus (HCV): a Potential Treatment to Prevent HCV Reinfection in Liver Transplant Patients, Journal of Virology, Mar. 2006, vol. 80, No. 6, pp. 2654-2664.
Holm, P. et al., Functional mapping and single chain construction of the anti-cytokeratin 8 monocloncal antibody TS1, Molecular Immunology 44 (2007) pp. 1075-1084.
Mariuzza, R.A. et al., The Structural Basis of Antigen-Antibody Recognition, Ann. Rev. Biophys. Biophys. Chem. 1987, vol. 16, pp. 139-159.
MacCallum, R.M. et al., Antibody-antigen Interactions; Contact Analysis and Binding Site Topography, J. Mol. Biol., 1996, vol. 262, pp. 732-745.
Gussow, D. et al., Humanization of Monoclonal Antibodies, Methods in Enzymology, 1991, vol. 203, pp. 99-121.
Oxford University Press, Virus Culture—A Practical Approach, ed. A.J. Cann, 2000, p. 84.
UNAIDS—AIDS Epidemic Update: Special Report on HIV Prevention—Dec. 2005.
Final Office Action issued for U.S. Appl. No. 12/524,816 filed Jul. 28, 2009 in the name of Roberto Burioni, mail date: May 9, 2012.
PCT International Search Report for PCT/IB2009/052212 filed on May 27, 2009 in the name of Roberto Burioni, et al.
PCT Written Opinion for PCT/IB2009/052212 filed on May 27, 2009 in the name of Roberto Burioni, et al.
Austin, F., et al., Antigenic mapping of an Avian H1 Influenza virus haemagglutinin and interrelationships of H1 virus from humans, pigs and birds, Journal Gen. Virol. 1986, 67: 983-992.
Asanuma, H., et al., Influenza PR8 HA-specific fab fragments produced by phage display methods, Biochemical and Biophysical Research Communication 2008, 366: 445-449.
Tkacova, M., et al., Evaluation of monoclonal antibodies for subtyping of currently circulating human type A viruses, Journal of Clinical Microbiology 1997, 35: 1196-1198.
Baca, M., et al., Antibody humanization using monovalent phage display, The Journal of Biological Chemistry 1997, 272: 10678-10684.
Burioni, R., et al., Dissection of human humoral immune response against Hepatitis C virus E2 glycoprotein by repertoire cloning and generation of recombinant fab fragments, Hepatology 1998, 28: 810-814.
Burioni, R., et al., A vector for the expression of recombinant monoclonal Fab fragments in bacteria, Journal of immunological Methods 1998, 217: 195-199.
Carter, P., et al., Humanization of an anti-p185HER2 antibody for human cancer therapy, PNAS 1992, 89: 4285-4289.
Cole, S., et al., A strategy for the production of human monoclonal antibodies reactive with lung tumor cell lines, Cancer Research 1984, 44: 2750-2753.
Low levels of influenza activity in Europe, EISS—Weekly Electronic Bulletin, Apr. 25, 2008.
Molinari, N., et al., The annual impact of seasonal influenza in the US: Measuring disease burden and costs, Vaccine 2007, 25: 5086-5096.
Perotti, M., et al., Identification of a broadly cross-reacting and neutralizing human monoclonal antibody directed against the Hepatitis C virus E2 protein, Journal of Virology 2008, 1047-1052.
Barbass, C., et al., Human primers for fab amplification: Original set, Phage Display Manual, 2004, CSH Press, 6-7.
Thompson, W., et al., Mortality associated with influenza and respiratory syncytial virus in the United States, JAMA 2003, 289: 179-186.
Ward, E., et al., Binding activities of a repertoire of single immunoglobulin variable domain secreted from *Escherichia coli*, Nature 1989, 341: 544-546.

Gunilla B. Karlsson Hedestam et al., The challenges of eliciting neutralizing antibodies to HIV-1 and to influenza virus, Microbiology, vol. 6, Feb. 2008, pp. 143-155.
Roberto Burioni et al., Molecular cloning of the first human monoclonal antibodies neutralizing with high potency Swine-origin Influenza A pandemic virus (S-OIV), New Microbiologica, vol. 32, 2009, pp. 319-324.
Gary A. Levy et al., Targeted Delivery of Ribavirin Improves Outcome of Murine Viral Fulminant Hepatitis via Enhanced Anti-Viral Activity, Hepatology, Mar. 2006, pp. 581-591.
Notice of Allowance issued in U.S. Appl. No. 12/524,816 filed on Jul. 28, 2009 in the name of Roberto Burioni, mailed on Oct. 4, 2012.
Restriction Requirement issued in U.S. Appl. No. 12/922,850 filed on Sep. 15, 2010 in the name of Roberto Burioni, mailed on Sep. 7, 2012.
Office Action issued in U.S. Appl. No. 13/141,071 filed on Jun. 20, 2011 in the name of Roberto Burioni, mailed on Nov. 19, 2012.
Restriction Requirement issued in U.S. Appl. No. 13/265,542 filed on Oct. 20, 2011 in the name of Roberto Burioni, mailed on Aug. 28, 2012.
Office Action issued in U.S. Appl. No. 13/265,542 filed on Oct. 20, 2011 in the name of Roberto Burioni, mailed on Oct. 25, 2012.
Dennis R. Burton, Antibodies, viruses and vaccines, Immunology, vol. 2, Sep. 2002, pp. 706-713.
Eduardo A. Padlan et al., Identification of specificity-determining residues in antibodies, The FASEB Journal, vol. 9, Jan. 1995, pp. 133-139.
Webster, Webster's New World Medical Dictionary, 2003, 2 pages.
Notice of Allowance issued in U.S. Appl. No. 13/265,542 filed on Oct. 20, 2011 in the name of Roberto Burioni, mailed on Mar. 22, 2013.
pcDNA 3.1(+), pcDNA 3.1(-) User Manual, Invitrogen, Version K, Nov. 10, 2010, 23 pages.
Merriam-Webster, Definition of Pathology, www.merriam-webster.com/dictionary/pathologies?show=0&t=1369438701, retrieved May 24, 2013, 4 pages.
Merriam-Webster, Definition of Syndrome, www.merriam-webster.com/dictionary/syndrome, retrieved May 24, 2013, 3 pages.
Wikipedia, Epitope mapping, en.wikipedia.org/wiki/Epitope_mapping, retrieved Jun. 4, 2013, 3 pages.
Allander, T., et al., Recombinant human monoclonal antibodies against different conformational epitopes of the E2 envelope glycoprotein of hepatitis C virus that inhibit its interaction with CD81, J Gen. Virol. 2000, 81 (Pt 10):2451-9.
Burioni, R., et al., Cross-reactive pseudovirus-neutralizing anti-envelope antibodies coexist with antibodies devoid of such activity in persistent hepatitis C virus infection, Virology 2004, 327:242-248.
Burioni, R., et al., Monoclonal antibodies isolated from human B cells neutralize a broad range of H1 subtype influenza A viruses including swine-origin Influenza virus (S-OIV), 2010, Virology, vol. 399, pp. 144-152.
Burton, Human primers for fab amplification: original set, Phage Display Manual, A1.6-A1.7, Cold Spring Harbor Laboratory, Cold Spring Harbor, NY 2001.
Burton, D.R., et al., Mouse primers for fab amplification, Phage Display Manual, A1.10, 2001, Cold Spring Harbor Laboratory, Cold Spring Harbor, NY 2001.
Mancini, N., et al., Modulation of Epitope-Specific Anti-Hepatitis C Virus E2 (Anti-HCV/E2) Antibodies by Anti-Viral Treatment, Journal of Medical Virology 2006, 78:1304-1311.
Matsuura, Y., et al., Characterization of Pseudotype VSV Possessing HCV Envelope Proteins, Virology 2001, 286:263-275.
Merriam-Webster, Definition of 'disparage', www.merriam-webster.com/dictionary/disparage, retrieved May 17, 2013, 3 pages.
Ribavirin—antiviral, Product Specification, Sigma-Aldrich, accessed Jan. 29, 2014, 1 page.
Rosa, D., et al., A quantitative test to estimate neutralizing antibodies to the hepatitis C virus: Cytofluorimetric assessment of envelope glycoprotein 2 binding to target cells, Proc. Natl. Acad. Sci. USA 1996, 93:1759-1763.
Vajdos, et al., Comprehensive Functional Maps of the Antigen-binding Site of an Anti-ErbB2 Antibody Obtained with Shotgun Scanning Mutagenesis, 2002, Journal of Molecular Biology, vol. 320, pp. 415-428.

(56) References Cited

OTHER PUBLICATIONS

Wikipedia. "Neutralizing antibody" Jan. 27, 2014. Web, en.wikipedia.org/wiki/Neutralizing_antibody.
International Preliminary Report on Patentability issued on Dec. 6, 2011 on Patentability for International Application PCT/IB2010/052434 filed on Jun. 1, 2010 in the name of Pomona Ricerca S.R.L.
International Preliminary Report on Patentability issued on Jun. 29, 2011 for International Application PCT/IB2009/055867 filed on Dec. 21, 2009 in the name of Pomona Ricerca S.R.L.
Non-Final Office Action mailed on May 21, 2014 for U.S. Appl. No. 12/922,850 filed on Sep. 15, 2010 in the name of Roberto Burioni et al.
Non-Final Office Action mailed on Jul. 26, 2013 for U.S. Appl. No. 12/922,850 filed on Sep. 15, 2010 in the name of Roberto Burioni et al.
Notice of Allowance mailed on Sep. 6, 2013 for U.S. Appl. No. 13/141,071 filed on Jun. 20, 2011 in the name of Roberto Burioni et al.
Final Office Action mailed on Jul. 25, 2013 for U.S. Appl. No. 13/141,071 filed on Jun. 20, 2011 in the name of Roberto Burioni et al.
National Center for Biotechnology Information. Retrieved on Dec. 30, 2014 from: <www.ncbi.nlm.nih.gov.>.
Morikawa, K., et al. *Translational enhancement of HCV RNA genotype 1b by 3'untranslated and envelope 2 protein-coding sequences*. Virology, vol. 345, pp. 404-415 (2006).
Creeke, P. I., et al. *Clinical Testing for Neutralizing Antibodies to Interferon-β in Multiple Sclerosis*. Ther. Adv. Neurol. Disorders, vol. 6(1), pp. 3-17 (2013).
Burioni, R., et al. *Anti-HIV-1 response elicited in rabbits by anti-idiotype monoclonal antibodies mimicking the CD4-binding site*. PLOS ONE, vol. 3, No. 10, e3423, pp. 1-7 (2008).
Hernandez, E., et al. *Compared protective effect of nasal immunoprophylaxis using a new human monoclonal IgM antibody, human polyclonal antibodies, F(ab')2, amantadine, and zanamivir for prophylaxis of influenza A virus pneumonia in mice*. Military Medicine, vol. 168, No. 3, pp. 246-251 (2003).
Burton, D.R., et al. *Vaccines and the induction of functional antibodies: Time to look beyond the molecules of natural infection?* Nature Medicine, vol. 6, No. 2, pp. 123-125 (2000).
Freeman, M.S. *The Role of Neutralizing Antibodies in MS Treatments*. Medscape Neurology: 5(2). (2003) 3 pgs.
Consumer Updates. *2009-2010 Seasonal Influenza Vaccines*. Published by the US Food and Drug Administration. Retrieved on Nov. 19, 2014 from: <http://www.fda.gov/ForConsumers/ConsumerUpdates/ucm100139.htm>.
Vaccines. Published by the National Institute of Allergy and Infectious Diseases accessed via WayBackMachine.com, Apr. 9, 2010. Retrieved on Nov. 25, 2014 from: <http://www.niaid.nih.gov/topics/vaccines/understanding/Pages/typesVaccines.aspx.>.
European Office Action issued by the EPO on Jun. 2, 2014 for EP Application No. 2274335 filed in the name of Pomona Ricerca SRL.

\* cited by examiner

SEQUENCE LISTING

```
<160> NUMBER OF SEQ ID NOS: 9

<210> SEQ ID NO 1
<211> LENGTH: 117
<212> TYPE: PRT
<213> ORGANISM: Artificial
<220> FEATURE:
<223> OTHER INFORMATION: Human or humanized antibody sequence

<400> SEQUENCE: 1

Leu Glu Ser Gly Gly Gly Leu Val Gln Pro Gly Gly Ser Leu Arg Leu
1               5                   10                  15
```

Ser Cys Ala Ala Ser Gly Ile Thr Phe Ser Ser Tyr Ala Met Ser Trp
            20                  25                  30

Val Arg Gln Ala Pro Gly Lys Gly Leu Glu Trp Val Ser Thr Val Asn
        35                  40                  45

Ser Gly Gly Gly Ser Thr Tyr Tyr Gly Asp Ser Val Arg Gly Arg Phe
    50                  55                  60

Thr Ile Ser Arg Asp Asn Ser Lys Ser Thr Leu Tyr Leu Gln Leu Asn
65                  70                  75                  80

Ser Leu Arg Ala Glu Asp Thr Ala Ile Tyr Tyr Cys Ala Lys Asp Lys
                85                  90                  95

Gly Arg Pro Ile Phe Gly Leu Val Thr Pro Ser Tyr Tyr Met Asp Val
            100                 105                 110

Trp Gly Asn Gly Thr
        115

<210> SEQ ID NO 2
<211> LENGTH: 100
<212> TYPE: PRT
<213> ORGANISM: Artificial
<220> FEATURE:
<223> OTHER INFORMATION: Human or humanized antibody sequence

<400> SEQUENCE: 2

Glu Leu Thr Gln Ser Pro Ser Ser Leu Ser Ala Ser Val Gly Asp Ser
1               5                   10                  15

Val Thr Ile Thr Cys Arg Thr Ser Glu Arg Ile Ser Thr Tyr Leu Asn
            20                  25                  30

Trp Tyr Gln Gln Lys Pro Gly Lys Ala Pro Arg Leu Leu Val Ser Gly
        35                  40                  45

Ala Ser Thr Leu Gln Gly Gly Val Pro Ser Arg Phe Ser Gly Ser Gly
    50                  55                  60

Ser Gly Thr Ala Phe Thr Leu Thr Ile Asn Ser Leu Gln Pro Glu Asp
65                  70                  75                  80

Phe Ala Thr Tyr Tyr Cys Gln Gln Ser Tyr Ser Thr Pro Leu Thr Phe
                85                  90                  95

Gly Gly Gly Thr
            100

<210> SEQ ID NO 3
<211> LENGTH: 351
<212> TYPE: DNA
<213> ORGANISM: Artificial
<220> FEATURE:
<223> OTHER INFORMATION: Human or humanized antibody cDNA sequence

<400> SEQUENCE: 3
ctcgagtctg ggggaggctt ggtacagcct ggggggtccc taagactctc ctgtgcagcc     60
tctggaatca catttagcag ctatgccatg agctgggtcc gccaggctcc agggaagggg    120
ctggagtggg tctcaactgt taacagtggt ggtggtagta catactacgg agactccgtg    180
aggggccggt tcaccatctc cagagacaac tccaagagca cgctgtacct gcaactgaac    240
agcctgagag ccgaggacac ggccatatat tactgtgcga agataagggt cgtccgatt    300 tttggactgg tcaccccatc atactacatg gacgtctggg gcaatgggac c            351

<210> SEQ ID NO 4
<211> LENGTH: 300
<212> TYPE: DNA

<213> ORGANISM: Artificial
<220> FEATURE:
<223> OTHER INFORMATION: Human or humanized antibody cDNA sequence

<400> SEQUENCE: 4

```
gagctcaccc agtctccatc ctccctgtct gcatctgtag agacagcgt caccatcact      60
tgtcggacaa gtgagagaat tagcacctat ttaaattggt atcagcagaa accagggaaa    120
gccctaggc tcctggtctc tggtgcatcc actttgcaag gtgggtccc atcaaggttc      180
agtggcagtg gatctgggac agctttcact cttaccatca cagtctgca gcctgaagat    240
tttgcaactt actactgtca acagagttac agtaccccac tcactttcgg cggagggacc  300
```

<210> SEQ ID NO 5
<211> LENGTH: 610
<212> TYPE: DNA
<213> ORGANISM: Influenza A virus

<400> SEQUENCE: 5

```
tgatcagaaa gcacacaaaa tgcaattgac gggatcagca acaaagtgaa ctcagtaatt    60
gagaaaatga acactcaatt cactgcagtg gcaaggagt tcaatgatct agaaaaaagg    120
attgagaatt tgaataagaa ggtcgatgat gggttttttgg atgtttggac atataatgct  180
gagttgctcg ttttgctcga gaacgaaagg actctagatt tccatgactt taacgtaaga  240
aatttatatg aaaaggtcaa atcacaattg agaaacaatg ccaaagaaat cgggaatggt  300
tgttttgagt ctatcacaa atgtgatgat gaatgcatgg agagcgtgaa gaatggcaca  360
tataactatc ccaaatattc araagaatcc aaattgaata gagaggaaat agacggtgtg  420
aaactagaat caatgggggt ttaccagatt ttggcgatct actccacagt cgccagttcc  480
ctggtcttgt tagtctccct gggggcaatc agcttctgga tgtgttctaa tgggtcattg  540
caatgcagaa tatgcattta agacttgaat ttcaaaatgt atggaaaaac cccttgttt   600
ctactaatac                                                         610
```

<210> SEQ ID NO 6
<211> LENGTH: 1698
<212> TYPE: DNA
<213> ORGANISM: Influenza A virus

<400> SEQUENCE: 6

```
atgaaggcaa acctactggt cctgttatgt gcacttgcag ctgcagatgc agacacaata    60
tgtataggct accatgcgaa caattcaacc gacactgttg acacagtact cgagaagaat   120
gtgacagtga cacactctgt taacctgctc gaagacagcc acaacggaaa actatgtaga  180
ttaaaggaa tagccccact acaattgggg aaatgtaaca tcgccggatg gctcttggga  240
aatccagaat gcgacccact gcttccagtg agatcatggt cctacattgt agaaacacca  300
aactctgaga tggaatatg ttatccagga gatttcatcg actatgagga gctgagggag  360
caattgagct cagtgtcatc attcgaaaga ttcgaaatat ttcccaaaga aagctcatgg  420
cccaaccaca acacaaacgg agtaacggca gcatgctccc atgaggggaa aagcagtttt  480
tacagaaatt tgctatggct gacgagaag gagggcycat acccaaagct gaaaaattct  540
tatgtgaaca aaaaagggaa agaagtcctt gtactgtggg gtattcatca cccgtctaac  600
agtaaggaac aacagaatct ctatcagaat gaaaatgctt atgtctctgt agtgacttca  660
aattataaca ggagatttac cccggaaata gcagaaagca ccaaagtaag agatcaagct  720
gggaggatga actattactg gaccttgcta aaacccggag acacaataat atttgaggca  780
```

```
aatggaaatc taatagcacc aatgtatgct ttcgcactga gtagaggctt tgggtccggc    840
atcatcacct caaacgcatc aatgcatgag tgtaacacga agtgtcaaac accccggga    900 gctataaaca gcagtctccc ttaccagaat atacacccag tcacaatagg agagtgccca    960
aaatacgtca ggagtgccaa attgaggatg gttacaggac taaggaacat tccgtccatt   1020
caatccagag gtctatttgg agccattgcc ggttttattg aagggggatg gactggaatg   1080
atagatggat ggtatggtta tcatcatcag aatgaacagg gatcaggcta tgcagcggat   1140 caaaaagca cacaaaatgc cattaacggg attacaaaca aggtgaacac tgttatcgag    1200
aaaatgaaca ttcaattcac agctgtgggt aaagaattca acaaattaga aaaaaggatg   1260
gaaaatttaa ataaaaaagt tgatgatgga tttctggaca tttggacata taatgcagaa   1320
ttgttagttc tactgaaaaa tgaaaggact ctggatttcc atgactcaaa tgtgaagaat   1380
ctgtatgaga aagtaaaaag ccaattaaag aataatgcca agaaatcgg aaatagatgt    1440 tttgagttct accacaagtg tgacaatgaa tgcatggaaa gtgtaagaaa tgggacttat   1500
gattatccca atattcaga agagtcaaag ttgaacaggg aaaaggtaga tggagtgaaa    1560
ttggaatcaa tggggatcta tcagattctg gcgatctact caactgtcgc cagttcactg   1620
gtgcttttgg tctccctggg ggcaatcagt ttctggatgt gttctaatgg atctttgcag   1680
tgcagaatat gcatctga                                                1698
```

```
<210> SEQ ID NO 7
<211> LENGTH: 565
<212> TYPE: PRT
<213> ORGANISM: Influenza A virus
<220> FEATURE:
<221> NAME/KEY: misc_feature
<222> LOCATION: (173)..(173)
<223> OTHER INFORMATION: Xaa can be any naturally occurring amino acid

<400> SEQUENCE: 7

Met Lys Ala Asn Leu Leu Val Leu Leu Cys Ala Leu Ala Ala Ala Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Lys Cys Asn Ile Ala Gly Trp Leu Leu Gly
65                  70                  75                  80

Asn Pro Glu Cys Asp Pro Leu Leu Pro Val Arg Ser Trp Ser Tyr Ile
                85                  90                  95

Val Glu Thr Pro Asn Ser Glu Asn Gly Ile Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Asn
    130                 135                 140

Thr Asn Gly Val Thr Ala Ala Cys Ser His Glu Gly Lys Ser Ser Phe
145                 150                 155                 160

Tyr Arg Asn Leu Leu Trp Leu Thr Glu Lys Glu Gly Xaa Tyr Pro Lys
                165                 170                 175

Leu Lys Asn Ser Tyr Val Asn Lys Lys Gly Lys Glu Val Leu Val Leu
```

```
                180             185             190
    Trp Gly Ile His His Pro Ser Asn Ser Lys Glu Gln Gln Asn Leu Tyr
        195                 200                 205
    Gln Asn Glu Asn Ala Tyr Val Ser Val Val Thr Ser Asn Tyr Asn Arg
        210                 215                 220
    Arg Phe Thr Pro Glu Ile Ala Glu Arg Pro Lys Val Arg Asp Gln Ala
    225                 230                 235                 240
    Gly Arg Met Asn Tyr Tyr Trp Thr Leu Leu Lys Pro Gly Asp Thr Ile
                    245                 250                 255
    Ile Phe Glu Ala Asn Gly Asn Leu Ile Ala Pro Met Tyr Ala Phe Ala
                260                 265                 270
    Leu Ser Arg Gly Phe Gly Ser Gly Ile Ile Thr Ser Asn Ala Ser Met
                275                 280                 285
    His Glu Cys Asn Thr Lys Cys Gln Thr Pro Leu Gly Ala Ile Asn Ser
                290                 295                 300
    Ser Leu Pro Tyr Gln Asn Ile His Pro Val Thr Ile Gly Glu Cys Pro
    305                 310                 315                 320
    Lys Tyr Val Arg Ser Ala Lys Leu Arg Met Val Thr Gly Leu Arg Asn
                    325                 330                 335
    Ile Pro Ser Ile Gln Ser Arg Gly Leu Phe Gly Ala Ile Ala Gly Phe
                    340                 345                 350
    Ile Glu Gly Gly Trp Thr Gly Met Ile Asp Gly Trp Tyr Gly Tyr His
                355                 360                 365
    His Gln Asn Glu Gln Gly Ser Gly Tyr Ala Ala Asp Gln Lys Ser Thr
                370                 375                 380
    Gln Asn Ala Ile Asn Gly Ile Thr Asn Lys Val Asn Thr Val Ile Glu
    385                 390                 395                 400
    Lys Met Asn Ile Gln Phe Thr Ala Val Gly Lys Glu Phe Asn Lys Leu
                    405                 410                 415
    Glu Lys Arg Met Glu Asn Leu Asn Lys Lys Val Asp Asp Gly Phe Leu
                    420                 425                 430
    Asp Ile Trp Thr Tyr Asn Ala Glu Leu Leu Val Leu Leu Glu Asn Glu
                435                 440                 445
    Arg Thr Leu Asp Phe His Asp Ser Asn Val Lys Asn Leu Tyr Glu Lys
                450                 455                 460
    Val Lys Ser Gln Leu Lys Asn Asn Ala Lys Glu Ile Gly Asn Arg Cys
    465                 470                 475                 480
    Phe Glu Phe Tyr His Lys Cys Asp Asn Glu Cys Met Glu Ser Val Arg
                    485                 490                 495
    Asn Gly Thr Tyr Asp Tyr Pro Lys Tyr Ser Glu Glu Ser Lys Leu Asn
                    500                 505                 510
    Arg Glu Lys Val Asp Gly Val Lys Leu Glu Ser Met Gly Ile Tyr Gln
                515                 520                 525
    Ile Leu Ala Ile Tyr Ser Thr Val Ala Ser Ser Leu Val Leu Leu Val
                530                 535                 540
    Ser Leu Gly Ala Ile Ser Phe Trp Met Cys Ser Asn Gly Ser Leu Gln
    545                 550                 555                 560
    Cys Arg Ile Cys Ile
                565

<210> SEQ ID NO 8
<211> LENGTH: 1701
<212> TYPE: DNA
<213> ORGANISM: Influenza A virus
```

<400> SEQUENCE: 8

```
atgaaggcaa tactagtagt tctgctatat acatttgcaa ccgcaaatgc agacacatta      60
tgtataggtt atcatgcgaa caattcaaca gacactgtag acacagtact agaaaagaat     120
gtaacagtaa cacactctgt taaccttcta aagacaagc ataacgggaa actatgcaaa      180
ctaagagggg tagccccatt gcatttgggt aaatgtaaca ttgctggctg atcctggga     240
aatccagagt gtgaatcact ctccacagca agctcatggt cctacattgt ggaaacacct     300
agttcagaca atggaacgtg ttacccagga gatttcatcg attatgagga gctaagagag     360
caattgagct cagtgtcatc atttgaaagg tttgagatat tccccaagac aagttcatgg     420
cccaatcatg actcgaacaa aggtgtaacg gcagcatgtc ctcatgctgg agcaaaaagc     480
ttctacaaaa atttaatatg gctagttaaa aaaggaaatt catacccaaa gctcagcaaa     540
tcctacatta atgataaagg aaagaagtc ctcgtgctat ggggcattca ccatccatct      600
actagtgctg accaacaaag tctctatcag aatgcagata catatgtttt tgtggggtca     660
tcaagataca gcaagaagtt caagccggaa atagcaataa gacccaaagt gagggatcaa     720
gaagggagaa tgaactatta ctggacacta gtagagccgg gagacaaaat aacattcgaa     780
gcaactggaa atctagtggt accgagatat gcattcgcaa tggaaagaaa tgctggatct     840
ggtattatca tttcagatac accagtccac gattgcaata aacttgtca acacccaag      900
ggtgctataa acaccagcct cccatttcag aatatacatc cgatcacaat ggaaaatgt      960
ccaaaatatg taaaaagcac aaaattgaga ctggccacag gattgaggaa tatcccgtct    1020
attcaatcta gaggcctatt tggggccatt gccggtttca ttgaagggg gtggacaggg     1080
atggtagatg gatggtacgg ttatcaccat caaaatgagc aggggtcagg atatgcagcc     1140
gacctgaaga gcacacagaa tgccattgac gagattacta caaagtaaa ttctgttatt     1200
gaaaagatga atacacagtt cacagcagta ggtaaagagt caaccaccct ggaaaaaaga    1260
atagagaatt taaataaaaa agttgatgat ggtttcctgg acatttggac ttacaatgcc     1320
gaactgttgg ttctattgga aaatgaaaga actttggact accacgattc aaatgtgaag    1380
aacttatatg aaaaggtaag aagccagcta aaaacaatg ccaaggaaat tggaaacggc     1440
tgctttgaat tttaccacaa atgcgataac acgtgcatgg aaagtgtcaa aatgggact     1500
tatgactacc caaaatactc agaggaagca aaattaaaca gaagaaaat agatggggta     1560
aagctggaat caacaaggat ttaccagatt ttggcgatct attcaactgt cgccagttca     1620
ttggtactgg tagtctccct gggggcaatc agtttctgga tgtgctctaa tgggtctcta    1680
cagtgtagaa tatgtattta a                                              1701
```

<210> SEQ ID NO 9
<211> LENGTH: 566
<212> TYPE: PRT
<213> ORGANISM: Influenza A virus

<400> SEQUENCE: 9

```
Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
```

```
            50                  55                  60
Ala Pro Leu His Leu Gly Lys Cys Asn Ile Ala Gly Trp Ile Leu Gly
 65                  70                  75                  80

Asn Pro Glu Cys Glu Ser Leu Ser Thr Ala Ser Ser Trp Ser Tyr Ile
                 85                  90                  95

Val Glu Thr Pro Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
            115                 120                 125

Glu Arg Phe Glu Ile Phe Pro Lys Thr Ser Ser Trp Pro Asn His Asp
            130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
                180                 185                 190

Leu Trp Gly Ile His His Pro Ser Thr Ser Ala Asp Gln Gln Ser Leu
                195                 200                 205

Tyr Gln Asn Ala Asp Thr Tyr Val Phe Val Gly Ser Ser Arg Tyr Ser
210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
                260                 265                 270

Ala Met Glu Arg Asn Ala Gly Ser Gly Ile Ile Ile Ser Asp Thr Pro
                275                 280                 285

Val His Asp Cys Asn Thr Thr Cys Gln Thr Pro Lys Gly Ala Ile Asn
            290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Ile Pro Ser Ile Gln Ser Arg Gly Leu Phe Gly Ala Ile Ala Gly
                340                 345                 350

Phe Ile Glu Gly Gly Trp Thr Gly Met Val Asp Gly Trp Tyr Gly Tyr
                355                 360                 365

His His Gln Asn Glu Gln Gly Ser Gly Tyr Ala Ala Asp Leu Lys Ser
            370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
                420                 425                 430

Leu Asp Ile Trp Thr Tyr Asn Ala Glu Leu Leu Val Leu Leu Glu Asn
                435                 440                 445

Glu Arg Thr Leu Asp Tyr His Asp Ser Asn Val Lys Asn Leu Tyr Glu
            450                 455                 460

Lys Val Arg Ser Gln Leu Lys Asn Asn Ala Lys Glu Ile Gly Asn Gly
465                 470                 475                 480
```

```
Cys Phe Glu Phe Tyr His Lys Cys Asp Asn Thr Cys Met Glu Ser Val
            485             490             495

Lys Asn Gly Thr Tyr Asp Tyr Pro Lys Tyr Ser Glu Glu Ala Lys Leu
            500             505             510

Asn Arg Glu Glu Ile Asp Gly Val Lys Leu Glu Ser Thr Arg Ile Tyr
            515             520             525

Gln Ile Leu Ala Ile Tyr Ser Thr Val Ala Ser Ser Leu Val Leu Val
        530             535             540

Val Ser Leu Gly Ala Ile Ser Phe Trp Met Cys Ser Asn Gly Ser Leu
545             550             555             560

Gln Cys Arg Ile Cys Ile
                565
```

MONOCLONAL ANTIBODIES HAVING HOMOSUBTYPE CROSS-NEUTRALIZATION PROPERTIES AGAINST INFLUENZA A VIRUSES SUBTYPE H1

CROSS REFERENCE TO RELATED APPLICATIONS

The present application is the US national stage of International Application PCT/IB2009/052212 filed on May 27, 2009 which, in turn, claims priority to Italian Application TO2008A000398 filed on May 27, 2008. The present application may also be related to International Application PCT/IB2008/050307 filed on Jan. 29, 2008 and its related US national phase Ser. No. 12/524,816 filed on Jul. 28, 2009 and to International Application PCT/IB2009/051068 filed on Mar. 16, 2009 and its related US national phase Ser. No. 12/922,850.

The present invention in general relates to the field of immunology.

More specifically, the invention concerns a monoclonal antibody directed against the H1-subtype HA (hemagglutinin) antigen of the influenza A virus, which is capable of recognizing and neutralizing both of strains isolated from man and strains isolated from animals.

The influenza viruses are capable of infecting different animal species, among which especially several avian, porcine and equine species. Only a few of these viruses have succeeded in adapting to man, i.e. infecting it and especially spreading itself from man to man. The main factor that allows for this adaptation is connected with the features of the most important surface protein of the virus, hemagglutinin. In particular, 16 subtypes (H1-H16) have been distinguished based on the antigenic features of this protein, and only three of these (H1, H2 and H3) have succeeded in adapting completely to man, becoming responsible for the three great influenza pandemics of the past century. Presently there are two subtypes circulating in man which cause the seasonal influenza epidemics, subtype H1 and subtype H3. The H1 subtype, recognized by the antibody that is the object of the present invention, appeared in man in 1918 causing the terrible pandemic designated as "Spanish influenza", named after the European country where the first cases were reported. Recent studies have demonstrated that the virus responsible for the "Spanish influenza" was an avian virus that infected birds, which, as a result of a few mutations, developed the ability to infect man and spread itself from man to man. The 1918 isolate is the common progenitor of all the H1-subtype viruses found in man and other animals, such as swine. The H1-subtype viruses were responsible for the annual human influenza epidemics until 1957, during which year they were displaced by a virus having an H2-subtype hemagglutinin, which has been responsible for the so-called "Asian" pandemic. No more cases caused by the H1 subtype were reported until 1977, during which year a few H1 isolates turned up again in Russia for reasons that are still non completely understood. Thus, nowadays H1-subtype viruses are still circulating, in association with H3-subtype viruses that appeared in man since 1967. For instance, notifications in Europe for the 2007-08 influenza season, within the period comprised between the 40$^{th}$ week of 2007 and the 16$^{th}$ week of 2008, evidenced that a good 30% of isolates were associated with an H1-subtype hemagglutinin (*European Influenza Surveillance Scheme—Weekly Electronic Bulletin—Apr. 28,* 2008).

The annual influenza virus epidemics have a considerable impact on the public health service and on the costs associated therewith. In the United States of America alone it is estimated that more than 200,000 people are hospitalized each year for syndromes connected to influenza viruses, with about 40,000 deaths more or less directly related thereto (Thompson et al., JAMA, 2003, 289:179-186). To these data we must add all the cases, in exponentially higher numbers, of infected subjects that do not go to work for more or less long periods, with inevitable economic repercussions due to the loss of working days. A recent work (Molinari et al., Vaccine, 2007, 25: 5086-5096) has estimated the medical costs directly related to annual influenza epidemics at 10.4 billions of US dollars per year, to which another 16.3 billions of US dollars must be added for lost earnings due to absence from work. If in the calculation we consider other items too, such as the monetization of the economical losses linked to the death of the infected subjects, the amount rises to the incredible figure of 87.1 billions of US dollars per year.

Currently, the only available tool for facing the annual influenza epidemics in some way is an inactivated trivalent vaccine containing H1- and H3-subtype viral isolate antigens (in addition to a B-type isolate), which presumably will be responsible for the epidemic of the next influenza season. This kind of prediction, based on epidemiological data linked to early isolations in some sentinel geographic areas, does not always turn out to be correct. Thus, there is a not at all negligible risk, which is present year after year, that the trivalent vaccine developed for a certain influenza season instead might prove substantially ineffective.

In that case, as well as in the case of a new pandemic, the only available prophylactic/therapeutic aid would be to resort to the two available classes of antiviral drugs: the M2 protein inhibitors (amantadine and rimantadine), and the neuraminidase inhibitors (oseltamivir and zanamivir). However, in this situation too, a series of problems can be already expected, related both to the need to administer the antivirals in a very early stage of the infection, and to the rapid appearance, which has already occurred however, of resistant viral isolates.

An alternative effective strategy could be based on neutralizing antibody preparations directed against critical viral proteins and capable of recognizing portions of such proteins which are shared among the different isolates of influenza viruses.

For a better understanding of the potential of an approach based on the passive administration of antibodies, it is useful to briefly mention the main structural features of the influenza viruses. The influenza viruses belong to the Orthomyxoviridae family and are characterized by the presence of an envelope derived from infected cell membranes, on which approximately 500 spikes are present, also referred to as projections. Such projections consist of trimers and tetramers from two important viral surface proteins, i.e. the aforementioned hemagglutinin (HA) and neuraminidase (NA), which is also used for the subtyping of type A viruses. An integral membrane protein (M2) is also found on the envelope surface, which protein is present in much lower numbers compared to hemagglutinin and neuraminidase, and also organized in tetramers.

The influenza virus is further characterized by the presence, within the core, of a segmented genome comprised of 8 single stranded RNA fragments. The three known influenza virus types are recognizable based on the features of some proteins within the virion (NP and M1): type A, type B, and type C. Those responsible for the annual epidemics are the type A and type B viruses. Instead, type C viruses are responsible for less severe syndromes.

The role of the surface proteins is essential in the viral replication cycle. In particular, hemagglutinin is the protein that allows the virus to recognize the sialic acid present on the surface of some cells, and to infect them. Instead, neuraminidase operates at the end of the viral replication cycle, that is during the release of new virus particles from the infected cells. Its function is to promote the release of hemagglutinin of the newly formed virions from the sialic acid present on the surface of the cell that produced them. The key role played by these two proteins, as well as their display on the virus surface, explain why they represent the main target of the immune response, and why they are susceptible to a high rate of mutation. In fact, the annual epidemics are caused by viruses that are more or less different from the ones of the previous years, and therefore are more or less effectively able to escape the immune response they stimulated. In other words, the progressive accumulation of point mutations in hemagglutinin (mostly) and neuraminidase (secondarily) makes the protective antibodies, produced in the course of previous epidemics, on the whole progressively ineffective.

The main protective role within the anti-influenza immune response is played by the humoral component. Antibodies exert their protective role primarily interfering with the binding of hemagglutinin to sialic acid, thereby preventing infection of the cells. Such a selective pressure determines the high rate of mutation in hemagglutinin. Within such a high variability, however, some unchanged amino acid residues have been found, indicative of their essential role in the function of the protein. These hemagglutinin portions represent a potential target for a cross-neutralizing response. However, it is predictable that such regions will not be able to induce an effective antibody response in most patients, in that the hiding of such targets in immunosilent areas has certainly represented a very favorable evolutionary step for the virus.

In view of the prophylactic and therapeutic aspect, it would be extremely useful to provide antibody molecules capable of recognizing such common regions within one subtype. Such antibodies could in fact represent a useful prevention tool when administered to subjects at risk, since they would be able to recognize a broad range of viruses of the same subtype but evolutionarily far away from one another, and thus would potentially be able to protect from most of the viruses belonging to such a subtype, including possible new viruses that acquire the ability to spread from animals to humans. This type of immunity, which is lost when the circulating isolates show a high rate of mutation compared to those of the previous years, is known as HOMOSUBTYPE ANTI-INFLUENZA IMMUNITY.

The present inventors have now succeeded in obtaining monoclonal antibodies with the above-mentioned desirable features.

Thus, a first aspect of the invention is a monoclonal antibody directed against the influenza A virus, which is able to bind a plurality of isolates, both human and animal, of the influenza A virus which express the H1-subtype hemagglutinin.

A second aspect of the present invention is a monoclonal antibody directed against the influenza A virus, characterized on that it has a neutralizing activity towards human and animal isolates of the H1-subtype influenza A virus. Preferably, such a neutralizing monoclonal antibody recognizes hemagglutinin (HA) of the H1-subtype influenza A virus as the antigen.

The monoclonal antibody of the invention is preferably human or humanized.

Such antibodies represent a valuable prevention tool when administered to patients at risk.

Moreover, the use of a human or humanized monoclonal antibody for human patients is a further advantage, in that the human or humanized antibody is certainly well tolerated.

In addition, by representing a component of the human antibody response to this virus, the monoclonal antibody of the invention constitutes a key factor for the design of innovatory vaccines that are able to induce an immunity that is extremely more effective, protective and broad-range towards the H1-subtype viruses, compared to the one induced by the presently used vaccines.

The steps that led to the attainment of the monoclonal antibody of the invention are described in detail in the experimental section that follows, which also illustrates its binding and neutralizing properties. The monoclonal antibody attainable by the procedure specifically described in the experimental section is a human antibody.

The preparation of humanized antibodies can be performed by any per se known methodology, as for example described in Baca et al, 1997 J. Biol. Chem 272:10678-84 or Carter et al, 1992, Proc. Natl. Acad. Sci 89:4285. Such bibliographic references are provided exclusively for illustration and not limitation. In fact, other methodologies for the preparation of humanized antibodies are known in the prior art and can be used within the present invention.

The attainment of one clone (designated as INF49) capable of producing monoclonal antibodies in the form of Fab fragments with the in vitro ability of binding multiple human and animal isolates from the H1-subtype influenza A virus is specifically described in the experimental section.

The monoclonal antibodies produced by clone INF49 (designated as Fab49) represent one preferred embodiment of the invention, as the inventors have experimentally proved that these antibodies display a neutralizing activity towards multiple human and animal isolates from the H1-subtype influenza A virus. For the sake of brevity, such an immunological property concerning the ability of neutralizing human and animal isolates from the H1-subtype influenza A virus will sometimes be referred to herein below as "homosubtype cross-neutralizing activity for subtype H1".

The sequence listing shows the amino acid sequence of the heavy chain variable domain (SEQ ID NO:1) and of the light chain variable domain (SEQ ID NO:2) of Fab49 of the invention. It further shows their respective encoding nucleotide sequences, designated as SEQ ID NO:3 and SEQ ID NO:4, respectively.

In particular, the experimental section describes the manufacture of the Fab49 monoclonal antibodies as Fab fragments. However, it is understood that the monoclonal antibodies can be manufactured and used in other forms too, such as for example whole immunoglobulins, or in the form of other types of antibody fragments, such as for instance $F(ab')_2$ fragments or antibody fragments smaller than Fabs (for example, single chain antibodies, single domain antibodies), as well as in the form of peptides at least 8 amino acids in length which have the same immunological properties as the Fab.

Single chain antibodies can be constructed according to the method described in U.S. Pat. No. 4,946,778 by Ladner et al., hereby included as reference. Single chain antibodies comprise the light and heavy chain variable regions linked by a flexible linker. The antibody fragment designated as single domain antibody is even smaller than the single chain antibody, as it comprises only one isolated VH domain. Techniques for obtaining single domain antibodies having, at least partially, the same binding ability as the whole antibody, are described in the prior art. Ward, et al., in "Binding Activities of a Repertoire of Single Immunoglobulin Variable Domains Secreted from *Escheria coli*," Nature 341:644-646, describes a screening method for obtaining the variable region of an antibody's heavy chain (VH single domain antibody) with a sufficient affinity for the target epitope to bind to it in an isolated form.

In the description that follows, the term "antibody" will then be used to refer to all the embodiments mentioned above, including whole immunoglobulins, Fab fragments or other antibody fragment types, single chain antibodies, single domain antibodies, etc.

The monoclonal antibodies of the invention may be generated and used in a free form or in a carrier-conjugated form. A carrier is any molecule or chemical or biological entity capable of conjugating with an antibody and making it immunogenic or increasing its immunogenicity. Non-limiting examples of carriers are proteins such as KLH (keyhole limpet hemocyanin), edestin, thyroglobulin, albumins as bovine serum albumin (BSA) or human serum albumin (HSA), erythrocytes such as sheep erythrocytes (SRBC), tetanus anatoxin, cholera anatoxin, polyamino acids such as for example poly(D-lysine:D-glutamic acid) and the like. In order to facilitate the binding of the antibody to the carrier, the antibody C-terminus or N-terminus may be modified, for example, by the insertion of additional amino acid residues, for instance one or more cysteine residues that are able to form disulfide bridges.

Because of its properties, which will be shown in detail in the experimental section that follows with reference to Fab49, the monoclonal antibody of the invention is particularly suited for use in medical applications, particularly in the manufacture of a medicament for the broad-range prophylactic or therapeutic treatment of H1-subtype influenza A virus infections.

Thus, the use of the monoclonal antibody of the invention for preparing a medicament for the prophylactic or therapeutic treatment of pathologies caused by H1-subtype influenza A virus infections, such as for instance the influenza syndrome, falls within the scope of the invention.

In this context too, the expression "Fab49 antibody" includes not only the Fab fragments but also any other form into which the antibody can be prepared, for example whole immunoglobulins, other kinds of antibody fragments, single chain antibodies, etc.

As described in detail in the experimental section, the present monoclonal antibody has been obtained by molecular biology techniques starting from an EBV-transformed human lymphocyte capable of producing human cross-reactive monoclonal antibodies, thus able to recognize MDCK (Madin-Darby canine kidney) (ATCC® n° CCL-34™) cell lysates infected with a few human reference isolates of the influenza A virus as referred to herein below, which express H1-subtype hemagglutinin: A/Puerto Rico/8/34 (ATCC® n° VR-1469™); A/Wilson-Smith/33 (ATCC® n° VR-1520); A/Malaya/302/54 (ATCC® n° VR-98). The antibody in question also resulted to be capable of recognizing NSK (Newborn swine kidney) (Istituto Zooprofilattico di Brescia) cell lysates infected with an animal-derived "field" isolate, and in particular swine-derived (SW1), as demonstrated by the sequence of the HA2 fragment of H1-subtype hemagglutinin expressed by it (SEQ ID NO:5).

A further particularly advantageous property of the monoclonal antibody of the invention is its ability to bind the recombinant HA protein from the A/California/04/2009 influenza virus isolate, recently identified as one of the isolates responsible for the so-called "swine influenza", officially designated as "new influenza" by the WHO.

Binding assays performed with the recombinant HA protein from the A/California/04/2009 isolate and the recombinant HA protein from the A/PR/08/1934 isolate, used as a positive control, are described in the following experimental section. The assays prove that the monoclonal antibody Fab49 of the invention is able to bind both of the recombinant HA proteins.

The performed assays further demonstrate that the monoclonal antibody Fab49 is able to neutralize HA protein pseudo-particles from both of the above-mentioned influenza virus isolates.

The specific procedures used for generating the transformed B cell lines from patients' peripheral blood are described in the following experimental section.

The procedures used for cloning the genes encoding the Fd portion of the heavy and light chains of the Fab49 antibody of the invention are also described, as well as those for producing them recombinantly, both as single peptides and Fab fragments.

The abilities of the monoclonal antibody of the invention to react with cells infected with different human and animal isolates from the H1-subtype influenza A virus were verified by ELISA and immunofluorescence. In addition, a neutralizing assay was carried out in order to verify the in vitro biological activity of the antibody. In this assay, the Fab49 antibody showed a homosubtype cross-neutralizing activity towards the human and animal type A and subtype H1 viral isolates as indicated above.

The obtained data indicate that the antibody of the invention is potentially effective in conferring a passive immunity towards the H1-subtype influenza A virus to the subjects to whom it is administered in one of the forms described, and its usefulness in the broad-range prophylaxis and therapy of pathologies caused by infection with the H1-subtype influenza A virus, such as for instance the influenza syndrome.

Thus, a further aspect of the invention is a pharmaceutical composition comprising an effective amount of the monoclonal antibody of the invention as the active ingredient and a pharmaceutically acceptable carrier and/or diluent. An effective amount is the one which is able to induce a favourable effect in the subject to which the composition is administered, for example to neutralize the H1-subtype influenza A virus.

In this context, the term "subject" designates any animal host to which the composition can be administered, including humans.

Non-limiting examples of pharmaceutically acceptable carriers or diluents usable in the pharmaceutical composition of the invention include stabilizers such as SPGA, carbohydrates (for example, sorbitol, mannitol, starch, sucrose, glucose, dextran), proteins such as albumin or casein, protein-containing agents such as bovine serum or skimmed milk, and buffers (for example phosphate buffer).

The monoclonal antibody of the invention can also be advantageously used as a diagnostic reagent in an in vitro method for the detection of anti-H1-subtype influenza A virus antibodies with identical or similar neutralizing properties in a biological sample previously obtained from a patient (such as for example a serum, plasma, blood sample or any other suitable biological material).

"Anti-influenza A virus antibodies with identical or similar neutralizing properties" are antibodies that display a homosubtype cross-neutralizing activity versus the human or animal H1-subtype influenza A virus. These antibodies may be found in the biological sample from the patient (or animal) as a result of a previous exposure to an influenza A virus, or because the patient had been previously administered with the monoclonal antibody of the invention for therapeutic or prophylactic or research purposes.

An assay method for detecting, in a biological sample previously obtained from a patient or an animal host, the presence of anti-influenza A antibodies having a homo-subtype cross-neutralizing activity towards the H1 subtype, comprising contacting the said biological sample with the monoclonal antibody of the invention, as a specific assay reagent, is thus included in the scope of the invention.

The assay can be qualitative or quantitative. The detection or quantification of the anti-H1-subtype influenza A virus antibodies having a homosubtype cross-neutralizing activity may be carried out by, for example, a competitive ELISA assay. Thus, a diagnostic kit comprising the monoclonal antibody according to the invention as a specific reagent is also within the scope of the invention, the said kit being particularly designed for the detection or quantification of anti-influenza A virus antibodies having a homosubtype cross-neutralizing activity towards the H1-subtype influenza A virus in a biological sample previously obtained from a patient or an animal host.

Similarly, the monoclonal antibody of the invention can be used as a specific reagent in an assay method for detecting or quantifying, in a previously prepared immunogenic or vaccine composition, epitopes capable of evoking, in the subject to which such a composition has been administered, anti-H1-subtype influenza A virus antibodies having neutralizing properties identical or similar to those of the monoclonal antibody of the invention, that is a homosubtype cross-neutralizing activity towards the H1-subtype influenza A virus.

Such a method is predicted to be useful for the assessment of any preparation to be used as a vaccine or immunogenic preparation, as the recognition by the monoclonal antibody of the invention could be indicative of the presence, in the immunogenic preparation and/or vaccine, of one or more epitopes capable of stimulating the production of antibody clones capable of recognizing an advantageous epitope, such as for example an epitope capable of eliciting a homosubtype immunity against the H1-subtype influenza A virus.

Finally, the monoclonal antibody of the invention may be used for preparing anti-idiotype antibodies according to methods per se known. Anti-idiotype antibodies are antibodies specifically directed towards the idiotype of the broad-range neutralizing antibodies used to prepare them, and as such are able to mimic the key epitopes they recognize.

Anti-idiotype antibodies directed against the monoclonal antibody of the invention are therefore included in the scope of the invention.

The following experimental section is provided purely by way of illustration and not limitation.

EXPERIMENTAL SECTION

Selection of the Patients

The patients enrolled in the study were selected so as to increase the chances of cloning therefrom cross-reactive anti-influenza antibodies, that is antibodies capable of recognizing, and potentially of neutralizing, different influenza virus isolates. In particular, it is described that some individuals, despite continuous exposure to the influenza virus (sometimes for professional reasons, as physicians, pediatricians, people working in kindergartens and schools), do not contract the disease. For this reason they were thought to be the best candidates for the generation of human monoclonal antibodies. In particular, the following inclusion criteria were obeyed:

between 25 and 55 years of age;
recent pathological medical history, for the ten years preceding the study, negative for clinical influenza syndromes;
antibody titer higher than 1:1000 against H1N1-subtype virus isolates, responsible for the annual epidemics during the five years preceding the study;
detectable neutralizing titer (IC50>=1:20) against two human reference H1N1-subtype virus A isolates (A/Puerto Rico/8/34; A/Malaya/302/54);
no prior anti-influenza vaccination;
compliance to receive anti-influenza vaccination.

At vaccination, and about 3 weeks post-vaccination, approximately 20 ml of blood were drawn from each patient into heparinized test-tubes.

Culture of the Reference Virus Isolates

MDCK (Madin-Darby canine kidney) cells (ATCC® no. CCL-34™) propagated in Modified Eagle Medium (MEM) (GIBCO), supplemented with 10% inactivated (treatment at 56° C. for 30 minutes) fetal bovine serum (FBS) (EuroClone), 50 µg/ml penicillin, 100 µg/ml streptomycin (GIBCO) and 2 mM L-glutamine (EuroClone) were used as the cell line. As for the field swine isolate SW1 (characterized in an unequivocal way by the HA2 region sequence attached to the patent application), NSK (Newborn swine kidney) cells (Istituto Zooprofilattico di Brescia) were used instead, which were treated similarly. The cells were incubated at 37° C. in a 5% $CO_2$ atmosphere and were passaged at a 1:3 ratio twice a week. For the experiments described in this patent application, the following H1N1-subtype influenza virus isolates were used: A/Puerto Rico/8/34 strain (ATCC® no. VR-1469™); A/Wilson-Smith/33 strain (ATCC® no. VR-1520), and A/Malaya/302/54 strain (ATCC® no. VR-98). With regard to H1N1 subtype, a swine-derived isolate (SW1) was also used, characterized on the basis of the sequence of the hemagglutinin HA2 portion (SEQ ID NO:5). Three other reference virus isolates were also used, two belonging to type A subtype H3N2 (A/Port Chalmers/1/73—ATCC® no. VR-810 and A/Aichi/2/68—ATCC® no. VR-547), and one belonging to type B (B/Lee/40—ATCC® no. VR-101). As the culture medium to grow the virus, MEM supplemented with 1 µg/ml serum-free trypsin (SIGMA) was used. The virus stocks were obtained from the culture supernatant as extracellular viruses. In short, after infecting the cells, the monolayer was observed daily to monitor the appearance of a cytopathic effect. Generally 4 days after the infection the supernatant was collected, centrifuged at 1000 RCF (relative centrifugal force) for 10 minutes to eliminate the cell debris and filtered with 0.22 µm filters (MILLIPORE). The supernatant was then aliquoted and stored at −80° C. as cell-free viruses.

Selection of Monoclonal Anti-Influenza Virus Antibodies from Peripheral Blood B Lymphocytes The production of monoclonal antibodies from patients was carried out by using a transformation method via infection with Epstein-Barr virus (EBV), previously described by Cole et al, 1984 Cancer Research 22:2750-2753. The supernatant from the different clones obtained was assessed for the presence of antibodies by ELISA. Clones capable of producing IgG antibodies in the supernatant which are able to react in the ELISA against the cell lysates infected with the above-mentioned three human isolates and the H1N1-subtype swine isolate SW1, but not against the ones infected with the two H3N2-subtype isolates and with the B isolate, were then selected for a subsequent characterization. In particular, MDCK cells were infected with the aforesaid isolates at a high multiplicity of infection. About 48 hours post-infection, the cells were detached from the flask and washed twice in PBS. The cell pellets were then suspended in 300 µl of lysis solution (100 mM NaCl, 100 mM Tris pH 8 and 0.5% Triton-X) and stored in ice for 20 minutes. The cell debris were centrifuged away at 10000 g for 5 minutes and the supernatant was stored at −20° C. as a protein extract. As for the preparation of the control antigen, non-infected cells were treated in the same way. The supernatant protein concentration was determined in duplicate using the BCA™ Protein Assay Kit (Pierce). Briefly, the sample protein dosage was determined by referring to a standard curve obtained by a series of known-concentration dilutions of bovine serum albumin (BSA). The absorbance of every sample was measured with a spectrophotometer at a wavelength of 540 nm. The lysates so obtained were then used (300 ng per well) to coat an ELISA plate (COSTAR) that was incubated at 4° C. overnight. The following day, the plate was washed with distilled water and blocked with PBS/1% BSA (Sigma) for 45 minutes at 37° C. Then, 40 µl of supernatant from each clone were added to each well, which were incubated for 1 hour at 37° C. After 5 washings (WASHER ETI-SYSTEM, DiaSorin) with PBS/0.5% Tween-20 (Sigma), 40 µl of peroxidase-conjugated anti-human Fc (1:4000 in PBS/1% BSA, Sigma) were added to each well and the plate was incubated for 1 hour at 37° C. After 5 more washings with PBS/0.5% Tween-20, 40 µl of TMB peroxidase substrate (Pierce) were added to each well. Approximately 15 minutes later, the enzymatic activity was blocked by adding 40 µl of $H_2SO_4$ and the signal was measured with a spectrophotometer set at 450 nm. In particular, one clone (designated as cINF49) proved to be able to produce antibodies capable of recognizing in a specific way all the lysates obtained from the cells infected with the different H1N1-subtype isolates, including the animal isolate. Instead, no signal was detectable in the cultures infected with the two H3N2-subtype viruses and in those infected with the B isolate.

Preparation of Fab Fragments from Clone cINF49

The genes encoding for the Fab49 chains were cloned into a prokaryotic expression vector.

This allows to avoid problems due to instability of antibody-producing cell clones, to better characterize the encoding genes from the molecular point of view, in order to have molecules that are certainly monoclonal at one's disposal, as well as increased amounts of the antibody itself.

The messenger RNA (mRNA) was extracted from the cultured cINF49 clone and reverse transcribed using an oligo-dT according to methods per se known. The cDNAs encoding the light chain and the Fd fragment (i.e. the heavy chain variable portion and the part of the constant portion present within the Fab fragment) were then amplified by described methods (CSH press, Phage display manual, ed. D. R. Burton, p. A1.6). The so obtained cDNAs were then cloned into an expression vector per se known, designated as RBCaf (Burioni et al, J. Imm. Meth, 1988). In short, the gene (amplified DNA) encoding the heavy chain Fd portion was digested with restriction enzymes XhoI and SpeI (Roche) for 1.5 hours at 37° C., and subsequently inserted into the vector's cloning site for heavy chains, in turn digested with the same enzymes. Instead, the light chain (amplified DNA) was digested with enzymes SacI and XbaI (Roche) and cloned into the vector similarly digested.

The so obtained recombinant construct was used to electrotransform *E. coli* strain XL1Blue (made competent by cold washings in glycerol), according to standardized protocols for the use of 0.2 cm cuvettes (Voltage: 2500 V; Capacitance: 25 µF; Resistance: 200Ω). In parallel, the DNA sequences of the light chain variable part and the heavy chain variable part were analyzed. The sequences are those provided in the Sequence Listing. The molecular analysis of the mutational pattern showed a picture ascribable to antigen-induced somatic mutation processes.

ELISA Assessment of Fab49 Obtained by Cloning into RBCaf 40 recombinant bacterial clones transformed with the Fab49 construct were analyzed by ELISA using crude lysates obtained by subjecting cultures to heat shock. In particular, clones of bacteria transformed with the construct were inoculated into 10 ml of SB medium containing ampicillin and tetracycline at the concentrations of 50 µg/ml and 10 µg/ml, respectively, and were grown under shaking at 37° C. until reaching an O.D. 600=1. Subsequently, a specific inducer (IPTG—isopropylβ-D-thiogalactopyranoside) was added at the final concentration of 1 mM and the culture was left shaking at 30° C. overnight. The cells were lysed by heat shock (3 freeze/thawing rounds, at −80° C. and 37° C., respectively) and then centrifuged to separate the cell debris from the Fab-containing supernatant. The soluble Fabs obtained were assayed by ELISA. 96-Well microtiter plates (Nunc) were coated with lysates from cells infected with the above-mentioned virus isolates. Lysates obtained from uninfected cells were used as a negative control. The ELISA plates coated with 300 ng of the lysates obtained as described were then left at 4° C. overnight. The next day, after removal of the unbound antigen, the plates were washed 5 times with PBS, and the unspecific binding sites were blocked with 3% albumin in PBS for 1 hour at 37° C. After removal of the blocking solution, the supernatants of the cell cultures treated as described above and containing the soluble Fabs were added thereto. This was followed by an incubation step at 37° C. for 2 hours. After 10 washing cycles with PBS/0.05% Tween 20, 40 µl of a 1:700 dilution of a polyclonal preparation of radish peroxidase-conjugated goat anti-human Fab immunoglobulins (Sigma) in PBS/1% BSA was added thereto. After a 1-hour incubation at 37° C. and a further series of 10 washes, the substrate (OPD-o-phenylenediainine) was added to the wells. The plates were then incubated for 30 minutes at room temperature in the dark. The reaction was quenched with 1N sulfuric acid and the optical density was assessed by spectrophotometric reading at 450 nm. All the assayed clones displayed a specific reactivity towards every lysate obtained from the cells infected with the H1N1-subtype viruses. One bacterial clone transformed with the expression vector containing the genes for the light chain and the heavy chain Fd fragment of Fab49 was thus selected. The selected bacterial clone was designated as INF49.

Purification of the Fab49 and Assessment of the Same by ELISA on Infected Cell Lysates The Fab produced from clone INF49 (from here on indifferently referred to as "clone" or "Fab") was thus immunoaffinity purified with columns composed of a sepharose resin containing the protein G (~2 mg/ml), to which a polyclonal preparation of goat antibodies capable of binding human Fabs (PIERCE, Illinois) was covalently linked. In short, one colony of clone INF49 was inoculated into 10 ml of SB medium containing ampicillin and tetracycline at the concentrations of 50 µg/ml and 10 µg/ml, respectively. The culture, which was grown overnight at 37° C., was sub-inoculated into a flask with 500 ml of SB added with the same concentration of antibiotics as before. The cells, subsequently induced by 1 mM IPTG, were left shaking overnight at 30° C. The culture was centrifuged at 5000 rpm for 25 minutes and the pellet resuspended in PBS was sonicated. A further centrifugation at 18,000 rpm for 25 minutes was necessary in order to remove the cell debris. The supernatant was filtered, and then it was slowly passed through the above-described sepharose column. Thereafter, the resin was washed with 10 PBS volumes, and finally the bound Fabs were eluted with an acidic solution (elution buffer—$H_2O$/HCl pH 2.2). The various fractions collected were neutralized with an appropriate solution (1M Tris pH 9) and concentrated by ultrafiltration (Centricon, Millipore). The purity of the purified Fab was assessed by running one aliquot on a 12% polyacrylamide/sodium dodecyl sulfate gel (SDS-PAGE). Finally, sequential dilutions of the purified Fab were assayed by ELISA as described. Into each plate, preparations of monoclonal Fabs directed against HCV E2 glycoprotein were included as negative controls. The results of this experiment confirmed those previously obtained with the bacterial lysates, confirming the specific reactivity of the clone towards the cells infected with H1N1-subtype viruses.

Immunofluorescence Assessment of Fab49 Obtained by Cloning into RBCaf

In order to confirm the data achieved by ELISA, Fab49 was also analyzed by an immunofluorescence assay. Briefly, the cells from the cultures infected with all the mentioned reference viruses were trypsinized and, after two washes in PBS, counted under a microscope with a hematocytometer. The cell suspension was thus used for the preparation of slides by centrifugation in a cytocentrifuge (Cytospin4, Shandon Southern Products) at 90 g for 3 minutes. The so prepared slides each contained a total of $2 \times 10^5$ cells. Control slides were prepared similarly with uninfected cells. The cells were then fixed and permeabilized at room temperature with a methanol-acetone solution (used at the temperature of $-20°$ C.) for 10 minutes. After 3 washes in PBS, the cells were incubated with Fab49 (100 µg/ml) for 30 minutes at 37° C. in a humid chamber and subsequently washed three times in PBS.

The cells were then incubated for 30 minutes at 37° C. in the humid chamber in the dark with a fluoresceine isothiocyanate-conjugated goat Fab (Sigma) diluted 1:200 in Evans Blue. The slides were examined under a fluorescence microscope (Olympus). A commercial mouse monoclonal (Argene) specific for the M1 influenza virus protein was used as a positive control. An antibody directed against the E2 glycoprotein of the hepatitis C virus (e509; Burioni et al, Hepatology, 1998) was used as a negative control. Fab49 showed, by immunofluorescence, a specific reactivity for all the cells infected with the human H1N1-subtype isolates, that is A/Puerto Rico/8/34 isolate, A/Wilson-Smith/33 isolate and A/Malaya/302/54 isolate. A similar result was obtained with the cells infected by the swine isolate SW1 used in the study. The fluorescence pattern displayed was clearly a cytoplasm-type pattern. Instead, no fluorescence was seen in uninfected cells, cells infected with H3N2-subtype virus and those infected with the B type isolate, or with the negative control antibody.

Neutralization Assay

In order to characterize the in vitro biological activity of the selected clone, a neutralization assay was designed for some of the reference virus isolates used in the study. In short, MDCK cells (NSK in the case of the swine isolate SW1) were seeded into MEM-10% FBS in a 96-well plate ($2 \times 10^4$ cells/well). Serial dilutions (from $10^{-1}$ to $10^{-8}$) of the virus stocks, obtained as described above, were prepared in maintenance medium (MEM with 2% FBS). Each dilution was repeated six times. When the cultured cells were confluent, the growth medium was removed and 100 µl of each of the virus dilutions were added to each well. After 1 hour at 37° C., the inocula were removed and 200 µl of MEM medium added with 1 µg/ml trypsin were placed into each well. The viral titer, expressed as $TCID_{50}$ (the dose that infects 50% of the cell culture), was calculated by applying Reed-Muench's formula:

$$TCID_{50} = \frac{\text{infectivity} > 50\% - 50\%}{\text{infectivity} > 50\% - \text{infectivity} < 50\%} \times \text{dilution factor}$$

In the light of the obtained data, the virus stock was diluted so as to use a multiplicity of infection (M.O.I.) of approximately 0.01 (1 virus particle per 100 cells) in the neutralization experiment. In the actual neutralization assay, the cells were seeded in a 24-well plate, with each well containing a sterile slide. The neutralization experiment was performed on 80%-90% confluent cells, i.e. about 48 hours after the seeding thereof. Dilutions of the purified Fab49 were then prepared, so as to attain final concentrations of 1 µg/ml, 5 µg/ml, 10 µg/ml and 20 µg/ml. Corresponding dilutions of the e509 anti-HCV antibody were prepared as a negative control. The various Fab concentrations were then incubated with the same volume of diluted virus stock (M.O.I.: 0.01) for 1 hour at 37° C. 250 µl of the virus-Fab mix were subsequently added to the wells containing the cells. A positive control for the infection was achieved by adding the culture medium alone to the virus stock. The plate was incubated for 1 hour at 37° C. in order to allow the non-neutralized virus to adsorb. The inoculum was then removed and the cells were washed twice with PBS. 1.5 ml of serum-free medium with 1 µg/ml trypsin were added to each well. After a 6-hour incubation at 37° C., the cell monolayer was washed with PBS and fixed with a cold methanol-acetone solution (1:2 ratio, stored at $-20°$ C.) for 10 minutes at room temperature. The fixed cells were washed and incubated with 250 µl of a commercial monoclonal anti-M1 antibody (Argene) for 30 minutes at 37° C. in a humid chamber. The cells were washed with PBS and finally incubated with a fluorescein-conjugated goat anti-mouse antibody, diluted in Evans blue, for 30 minutes at 37° C. in a humid chamber in the dark. After three washes in PBS, the slides were finally examined under a fluorescence microscope. The neutralizing activity of Fab49 was determined by counting the single positive cells and calculating the percentage decrease in the number of infected cells, compared to the positive control infected with the virus alone. The neutralization assays were carried out in three separate sessions for each of the isolates used for the neutralization assays (see FIGS. 1-3). In each experiment, the different Fab49 dilutions were repeated in triplicate, similarly to what performed for the negative (Fab e509 anti-E2/HCV) and positive (virus and Fab-free medium) controls of infection.

The Fab produced by clone INF49 showed a homotype cross-neutralizing activity against human and animal H1N1-subtype virus A isolates. Instead, no reduction was detected in the infecting ability of the two H3N2-subtype viruses and of type B virus used in the study, confirming the specificity of the homosubtype neutralizing activity observed for subtype H1N1. In particular, the Fab produced by clone INF49 (called Fab49) showed an $IC_{50}$ (the Fab concentration that inhibits 50% of infection by the virus isolate assayed) below 5 µg/ml for each of the H1N1-subtype isolates assayed, i.e. a concentration that is easily obtainable by an in vivo administration of the molecules in question even without taking into account the usually considerable increase in the neutralizing biological activity observed when Fabs are converted into the whole immunoglobulin form, one of the possible pharmaceutical formulations included within the scope of the invention.

FIGS. 1 to 3 summarize the results obtained with Fab 49, produced by clone INF49, in the different neutralization sessions performed on the various H1N1-subtype influenza virus isolates used in the study.

Particularly, FIG. 1 is a graph that illustrates the neutralization percentage of the virus A/Puerto Rico/8/34 by different Fab 49 concentrations. The results obtained with the human e509 anti-HCV Fab are reported as a negative control.

Figure 1:
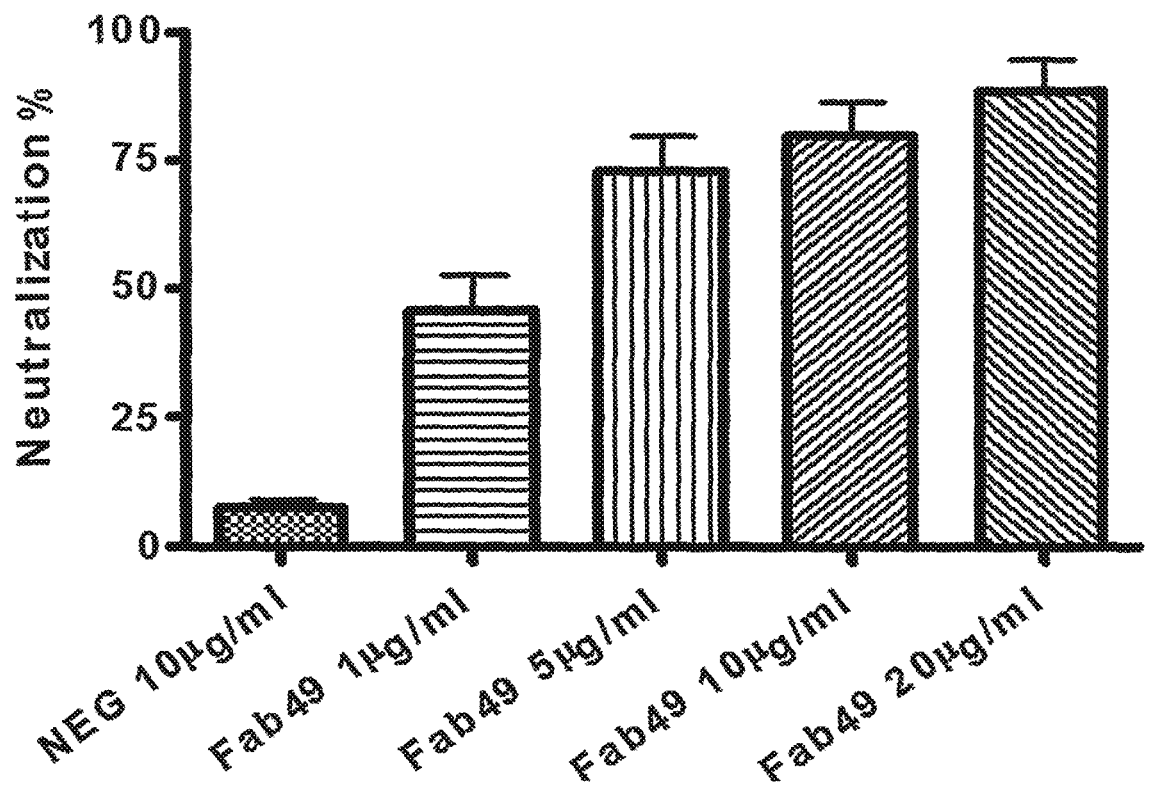
Figure 2:
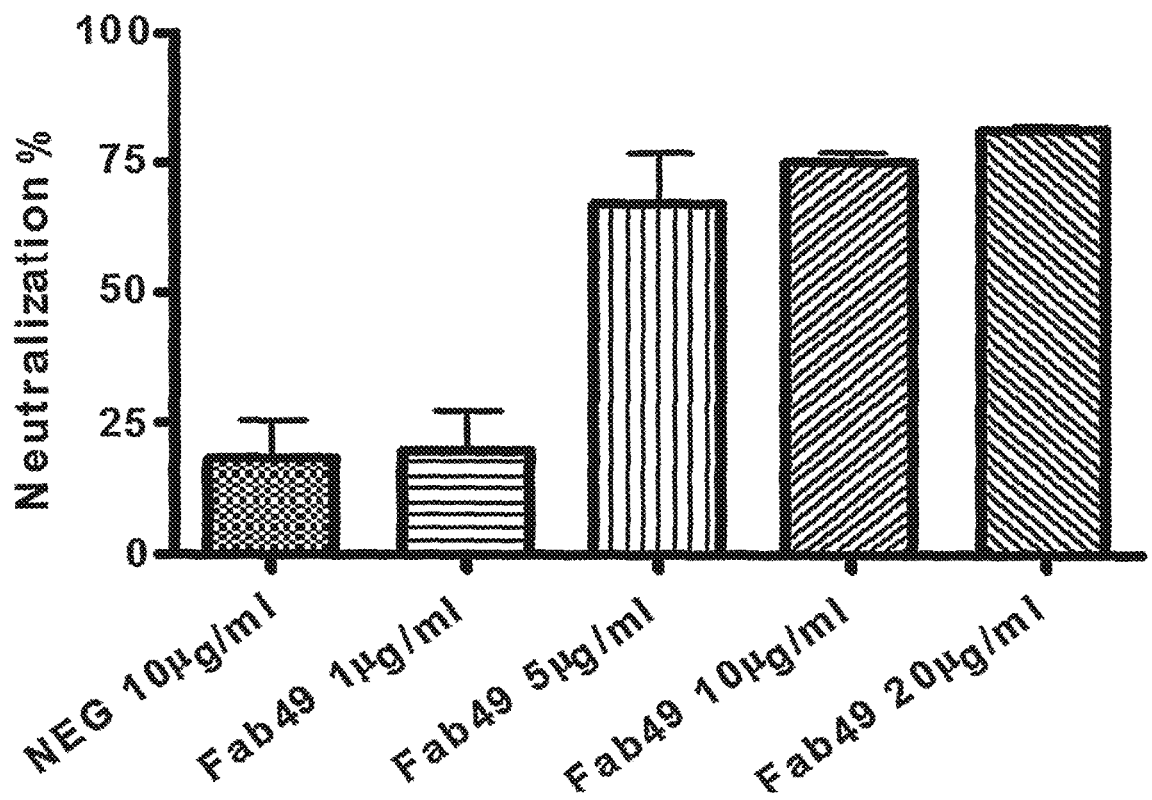
FIG. 2 is a graph that illustrates the neutralization percentage of the A/Wilson-Smith/33 isolate by different Fab 49 concentrations. The results obtained with the human e509 anti-HCV Fab are reported as a negative control.
Figure 3:
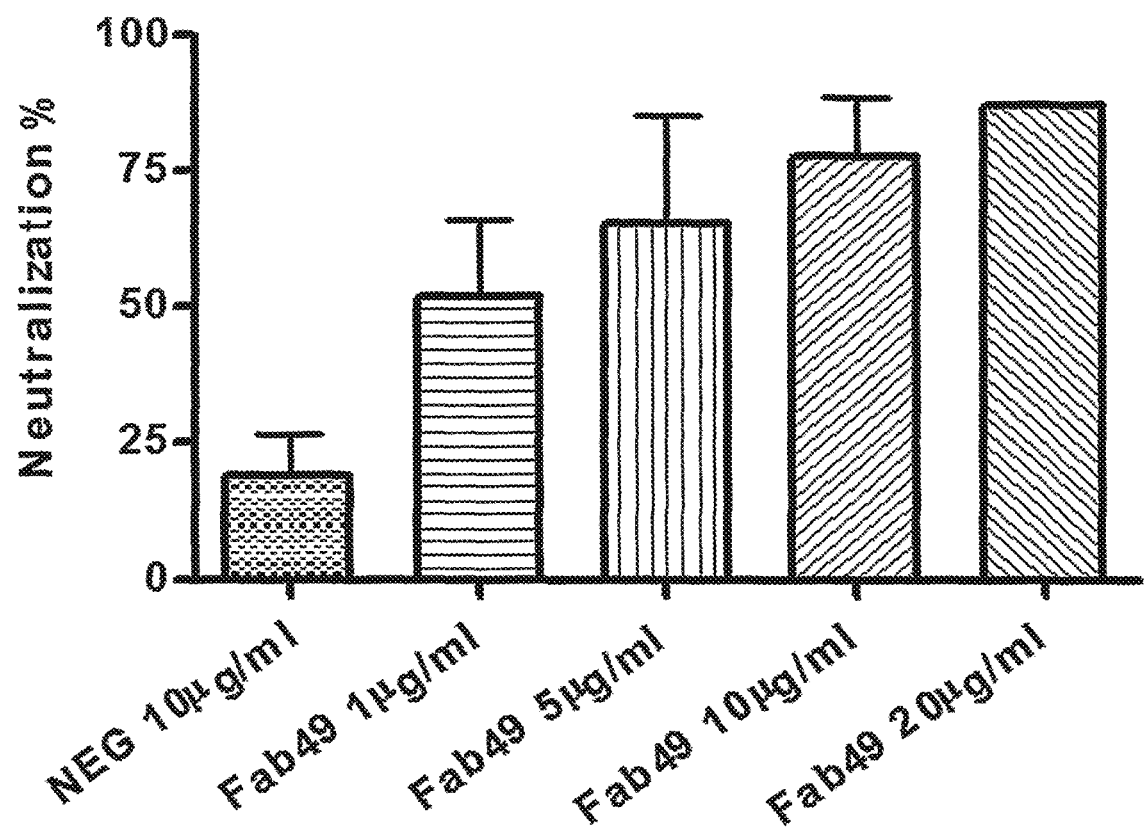
FIG. 3 illustrates the neutralization percentage of the field swine isolate SW1 used herein by different Fab 49 concentrations. The results obtained with the human e509 anti-HCV Fab are reported as a negative control.

Characterization of the Antigen Recognized by Fab49: Western Blot on a Lysate from Infected Cells 10 μg of a cell lysate infected with the A/Puerto Rico/8/34 isolate, prepared as described earlier, were run under native conditions on a 10% polyacrylamide gel. For this purpose, the samples were run at 100V for 1 hour in a proper refrigerated tank (BIORAD). Thereafter, the gel was removed from the electrophoresis apparatus and incubated for 10 minutes in Transfer Buffer (Tris base 3 g; Glycine 14.41 g, $dH_2O$ 800 ml, Methanol 200 ml) in order to eliminate any detergent residue. The transfer onto a nitrocellulose membrane (Hybond-ECL; Amersham Biosciences) was then carried out overnight at 30V and 90 mA. The membrane was then blocked for 1 hour with 5% dried milk dissolved in 1×PBS and thereafter washed three times in 1×PBS—0.1% Tween. During each wash, the membrane was left shaking on a swinging platform for 10 minutes. After which, the different Fabs, diluted in PBS with 5% dried milk, were added at the concentration of 5 μg/ml. Besides Fab49, the following controls were added: e509 as a negative control; commercial mouse anti-HA whole IgG1 (COVANCE); commercial mouse anti-M1 whole IgG1 (ARGENE); mouse anti-M2 whole IgG1 (ABCAM); human serum diluted 1:200. Each antibody was left shaking for 1 hour at room temperature. Thereafter, the membrane was washed again in PBS as described earlier. The same secondary mouse (1:1000) or human (1:2000) antibodies as described for the ELISA assay were then added, depending on the source of the antibody to be detected. For the detection of the signal, a working solution was prepared by mixing two substrates (SuperSignal® West Pico Chemiluminescent Substrate Pierce) in a 1:1 ratio, being particularly careful not to expose it to sources of light. The nitrocellulose membrane was incubated for 5 minutes with the working solution and then removed and mounted in a HyperCassette (AMERSHAM). This was developed on a Kodak film in the dark room after the necessary exposure time. The described assay was performed in two different sessions, and in each of them the membrane portion incubated with Fab49 showed the presence of a band weighing slightly less than 80 KDa, consistent with the weight of the immature form of the viral hemagglutinin (HA0). This was confirmed by the same band being also displayed on the strip incubated with the anti-hemagglutinin control antibody. An analogous band, more intense than the others, was also detected in the membrane portion incubated with human serum. The result of this experiment shows that the antibody is directed against the influenza virus hemagglutinin, perfectly consistent with the neutralization data, since hemagglutinin is known to be the main target of the humoral neutralizing response.

Binding and Neutralization Assays for HA from the Subtype A Influenza (H1N1) (Swine Influenza)

The HA proteins of the influenza viruses A/PR/08/1934 and A/California/04/2009 were amplified, respectively, from the supernatant of MDCK cells infected or synthesized in vitro (GenART, Ragensburg, Germany) and were cloned into pcDNA3.1 expression vectors (Invitrogen), thereby obtaining one construct H1 HA (A/PR/08/1934) and one construct H1 HA (A/California/04/2009).

The cDNA and amino acid sequences of the HA proteins of the two above-indicated isolates are displayed in the sequence listing as SEQ ID No: 6 (cDNA sequence of the HA protein from A/PR/08/1934), SEQ ID No: 7 (amino acid sequence of the HA protein from A/PR/08/1934), SEQ ID No: 8 (cDNA sequence of the HA protein from A/California/04/2009) and SEQ ID NO: 9 (amino acid sequence of the HA protein from A/California/04/2009), respectively.

Human epithelial kidney (HEK) 293T cells were transfected with 3 μg of the recombinant vector pcDNA3.1 containing the construct H1 HA (A/PR/08/1934) or the construct H1 HA (A/California/04/2009). After centrifugation and fixation, the transfected cells were incubated with Fab49 (10 μg/ml). After further washes, the cells were incubated with a FITC-conjugated human anti-Fab monoclonal antibody and assayed by FACS. The data were analyzed as described by Perotti et al., J Virology, 2008 January; 82(2):1047-52. The experiment demonstrated that Fab49 recognizes 293T cells transfected with either of the recombinant vectors.

For the neutralization assay, retrovirus vectors modified so as to express influenza HA proteins on their pericapsid (pseudo-typing), including the reporter gene Luc, were produced from 293T cells co-transfected with FuGene 6 (Roche) and the following plasmids: Luc system (5 μg pCMVΔR8.2 and 5.5 μg pHR'CMV-Luc) plus 3 μg of construct H1 HA (A/PR/08/1934) or H1 HA (A/California/04/2009). The supernatants were collected 48 hours after the transfection, filtered through a 0.45 μm low protein-binding filter and used immediately or frozen at −80° C. The titers of the HA pseudotypes were measured on 293T and MDCK cells. Briefly, 48 hours after infection of the cells with 100 μl of the lentivirus Luc HA-pseudotyped vector (HA-Luc) at different dilutions, the cells in 96-well plates were lysed in a Luc assay cell lysis buffer (luciferase assay reagent, Promega) according to the manufacturer's instructions. The titers of the pseudo-types have been expressed as relative luminescence units (RLU/ml).

Fab49's neutralization activity was tested by using a neutralization assay based on influenza pseudo-particles. This approach showed that Fab49 has a strong neutralization activity towards all the influenza virus pseudo-particles generated with the two H1N1-subtype isolates (A/PR/08/1934 and H1 HA (A/California/04/2009), with an [IC50] of approximately 2 μg/ml.

The invention claimed is:

1. A prokaryotic expression vector comprising nucleotide sequence SEQ ID NO:3, or nucleotide sequence SEQ ID NO:4, or both the nucleotide sequences SEQ ID NO:3 and SEQ ID NO:4.

2. An isolated host cell transformed with the expression vector according to claim 1.

* * * * *